United States Patent [19]

Abe et al.

[11] Patent Number: 4,525,265

[45] Date of Patent: Jun. 25, 1985

[54] ELECTROCHEMICAL SENSOR CAPABLE OF DETERMINING HYDROGEN PEROXIDE CONCENTRATION AND ANALYZER USING THE SAME

[75] Inventors: Yumiko Abe, Hitachi; Kenji Yasuda, Tokyo, both of Japan

[73] Assignee: Hitachi, Ltd., Tokyo, Japan

[21] Appl. No.: 571,947

[22] Filed: Jan. 19, 1984

[30] Foreign Application Priority Data

Jan. 21, 1983 [JP] Japan ................................. 58-7333

[51] Int. Cl.$^3$ ............................................ C12Q 1/58
[52] U.S. Cl. ................................. 204/403; 204/412; 204/415; 204/435; 435/817
[58] Field of Search ............... 204/403, 415, 1 E, 412, 204/435; 435/817; 128/635

[56] References Cited

U.S. PATENT DOCUMENTS

| | | | |
|---|---|---|---|
| 3,770,607 | 11/1973 | Williams | 204/403 |
| 3,900,382 | 8/1975 | Brown | 204/403 |
| 3,966,579 | 6/1976 | Chang et al. | 204/415 X |
| 4,073,713 | 2/1978 | Newman | 204/403 |
| 4,390,405 | 6/1983 | Hahn et al. | 204/415 |

*Primary Examiner*—G. L. Kaplan
*Attorney, Agent, or Firm*—Antonelli, Terry & Wands

[57] ABSTRACT

A urea-determining sensor and a glucose-determining sensor are arranged to face a single passage through which a sample flows. The urea sensor combines a membrane of immobilized urease with an ammonium ion-selective electrode. The glucose sensor consists of a layer of immobilized glucose oxidase and a polarographic electrode having a hydrogen peroxide-permeable layer. The latter sensor incorporates a work electrode and a counter electrode, and determines the concentration of hydrogen peroxide that permeates therethrough from the intensity of electric current that flows between the two electrodes. The counter electrode of the glucose sensor is formed of metallic palladium. The specific counter electrode material eliminates the problem of silver dissolution into the flow passage and extends the life of the urea sensor.

11 Claims, 5 Drawing Figures

ELECTROCHEMICAL SENSOR CAPABLE OF DETERMINING HYDROGEN PEROXIDE CONCENTRATION AND ANALYZER USING THE SAME

BACKGROUND OF THE INVENTION

This invention relates to an electrochemical sensor capable of determining hydrogen peroxide concentrations in materials and also to an analyzer which uses such a sensor together with a different sensor.

Enzyme electrode sensors and electrochemical sensors for determining hydrogen peroxide concentrations in samples, provided with an immobilized membrane of oxidase that evolves hydrogen peroxide by an enzyme reaction, are equipped with membranes that permeate hydrogen peroxide. Sensors of these types, which detect hydrogen peroxide polarographically, are known, for example, from U.S. Pat. No. 4,240,889. A sensor typical of these types comprises a work electrode and a counter electrode, the former being usually formed of gold or platinum and the latter, of silver. It is common with such a sensor that the reaction

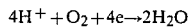

$$4H^+ + O_2 + 4e \rightarrow 2H_2O$$

takes place at its counter electrode.

This reaction exhibits a relatively stable potential when the electrode is made of silver, and merely applying a constant voltage to the silver counter electrode makes controlled potential electrolysis possible. For this reason counter electrodes of silver are preferred.

Attempts have been made to arrange an electrochemical sensor capable of detecting hydrogen peroxide together with another electrochemical sensor with a different purpose in a common flow passage. The latter may be, for example, an electrochemical sensor for urea-nitrogen determination equipped with a urease-immobilized-enzyme membrane. The urea-nitrogen-detecting sensor decomposes urea in the sample with ammonia and determines the resultant with the aid of an ammonium ion-selective electrode.

We have found that the urea-nitrogen-detecting sensor can seriously deteriorate in performance when it is located near another sensor in the same flow passage.

SUMMARY OF THE INVENTION

It is an object of this invention to prevent the deterioration in performance of a urea-nitrogen-detecting sensor while in use along with a different sensor.

Another object of the invention is to improve an $H_2O_2$ electrode which can otherwise deactivate urease.

Yet another object of the invention is to provide an electrode material for a hydrogen peroxide-detecting sensor from which silver will not dissolve out.

A further object of the invention is to provide an electrochemical sensor having a counter electrode which will not bring any drift to the measured value.

The present invention is based on the discovery that the cause for the deterioration of a urea-nitrogen sensor is the fact that the silver forming the counter electrode of an electrochemical sensor capable of determining a hydrogen peroxide content, such as a glucose sensor, dissolves out into the flow passage and deactivates the urease of the urea-nitrogen sensor.

In accordance with the present invention, the electrochemical sensor capable of determining hydrogen peroxide contents is of a type in which a constant potential is applied between its work electrode and counter electrode, the latter being made of a palladium-containing metallic material. This construction eliminates the unfavorable affect of silver.

The expression "electrochemical sensor capable of determining hydrogen peroxide contents" as used herein embraces any of the hydrogen peroxide-determining sensors equipped with a hydrogen peroxide-permeable membrane and also the enzyme sensors combining such a hydrogen peroxide-determining sensor with an oxidase-immobilized membrane. The enzyme sensors include, for example, glucose sensors using glucose oxidase, galactose sensors using galactose oxidase, and lactic acid sensors using lactic acid oxidase. They invariably determine the amount of hydrogen peroxide produced by an enzyme reaction.

The term "urea-nitrogen sensor" as used herein means a sensor provided with urease-immobilized enzyme and which uses the reaction in which urea is decomposed into ammonia. By "palladium-containing metallic material" is meant metallic palladium itself or any palladium alloy.

Although metallic palladium is used in preferred embodiments of the invention to be described later, palladium alloys may be employed instead to attain comparable effects. However, counter electrodes formed of platinum and platinum black, which are deemed similar in properties, were not useful in practice because of prolonged drifts. The present invention is applicable to uric acid and cholesterol sensors using an immobilized membrane of oxidase as well as to the glucose sensor described above.

DETAILED DESCRIPTION OF THE PREFERRED EMMBODIMENTS

Figure 1:
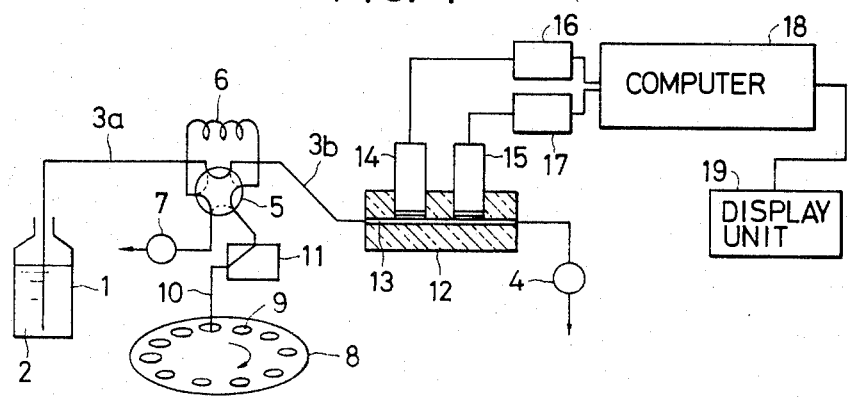
FIG. 1 is a flow chart of an embodiment of the invention.

Referring to FIG. 1, there are shown a hydrogen peroxide-detecting sensor 14 and a urea-nitrogen-detecting sensor 15 arranged in parallel along a flow passage 13 formed in a flow cell body 12, with the membranes of both of the sensors facing the passage 13. The sensors 14 and 15 are connected, respectively, through amplifiers 16 and 17 to a computation and control unit 18. The urea-nitrogen sensor 15 comprises an ammonium ion-selective electrode equipped with an enzyme membrane of immobilized urease as an outer layer. It decomposes urea in a given sample with the urease into ammonia and determines the ammonia ions thus produced.

A sampler 8 consisting of a turntable carries in an orderly manner a number of sample containers 9 each containing a blood sample. A nozzle 10, controlled by a selector valve 5, is raised and lowered by a lifting mechanism 11. A buffer solution 2 from a reservoir 1 is introduced into the flow cell 12 via lines 3a, 3b. The selector valve 5 is associated with a metering pipe 6. When the valve 5 is in the full-line position, the buffer solution 2 is led into the flow cell 12 by a pump 4. In this state another pump 7 is actuated to conduct a predetermined amount of the blood sample from a sample container 9, already shifted to a suction position, through the nozzle 10 into the metering pipe. Next, the selector valve 5 is shifted to the broken-line position, and the sample in the metering pipe 6 is guided by the buffer solution into the line 3b and thence into the flow cell 12, following dilution with the buffer solution to a predetermined ratio. The hydrogen peroxide concentration detected by the hydrogen peroxide-determining sensor 14 and the urea-nitrogen concentration detected by the urea-nitrogen-determining sensor 15 are both shown as detection outputs on a display unit 19.

Figure 2:
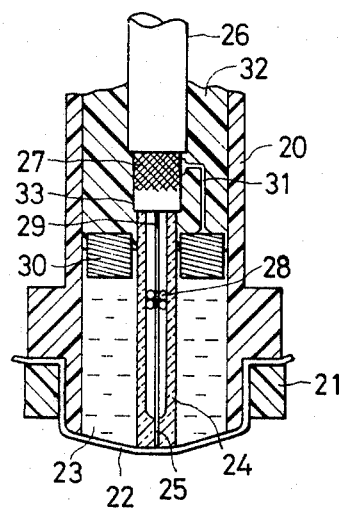
FIG. 2 is a partial sectional view of a hydrogen peroxide-determining sensor.

FIG. 2 shows the construction details of the hydrogen peroxide sensor 14 used in the embodiment of FIG. 1. A work electrode 25 consists of a platinum wire 0.1 mm in diameter, mostly sealed in a glass tube 24. The tip of the electrode 25 is in contact with a hydrogen peroxide-permeable membrane. In a cylindrical body 20 of acrylic resin is disposed a ring-shaped counter electrode 30, which is formed of metallic palladium. The hydrogen peroxide-permeable membrane 22 is attached to the electrically insulating body 20 with a ring-shaped fixing collar 21, so that it covers one end of the cylindrical body 20. The space between the work electrode 25 and the counter electrode 30 in the body 20 is filled with a potassium chloride (KCl) electrolyte with a concentration of 1M. The work electrode 25 is connected to the core wire of a coaxial cable 26, whereas the counter electrode 30 is connected to the meshed wire shield of the cable with a counter electrode lead 31. The wire shield 27 surrounds the outer surface of a covering 33 of the cable. A work electrode lead 29 is connected to the work electrode 25 through a holder 28. The space around the end portion of the cable 26 and the counter electrode lead 31 is packed with hydrophobic epoxy resin 32. Thus, the end portion of the body 20 where the cable is drawn out is sealed with the hydrophobic resin. When the electrochemical sensor shown in FIG. 2 is used as a hydrogen peroxide-determining sensor, a voltage of +0.6 V is applied to the work electrode.

With the embodiment using the sensor of FIG. 2, there occurred practically no deactivation of urease except by the elimination of the immobilized enzyme. The embodiment thus achieved an improvement in that it avoided the deterioration of the urea sensor from its use in combination with the hydrogen peroxide sensor. In a comparative experiment in which the hydrogen peroxide sensor was combined with a conventional silver-silver chloride counter electrode, the urea sensor was found deactivated on the second day, and determination in the practical sense became difficult within about one week.

When a conventional silver-silver chloride counter electrode was used and a voltage of +0.6 V was applied to the work electrode, the time required for substantial stabilization of the base line after initiation of voltage application was about 60 minutes. With the embodiment of the invention the corresponding time was about 20 minutes, and the initial stabilization time was markedly shortened. Moreover, the flucturation of the base line was less for a longer period of time than with the conventional arrangements. The curve a in FIG. 3 represents a working curve of hydrogen peroxide concentration in the blood, indicating very good linearity.

Figure 4:
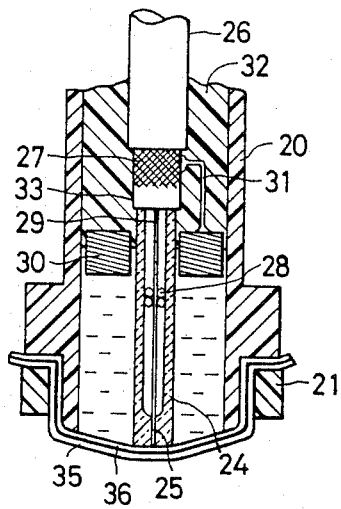
FIG. 4 is a partial sectional view of a glucose-determining sensor.

Another embodiment of the invention will now be described. In place of the hydrogen peroxide sensor 14 of FIG. 1, a glucose-determining sensor as shown in FIG. 4 was used. The sensor was constructed in the same way as that shown in FIG. 2 except that the hydrogen peroxide-permeable membrane comprised an outer layer 35 and an inner layer 36. The inner layer 36 was permeable to hydrogen peroxide, and the outer layer contained immobilized glucose oxidase. Such two layers may be either integrally formed together or separately formed and combined together. The hydrogen peroxide produced by the enzyme reaction of glucose oxidase was detected by the sensor as it passed through the inner layer, and the glucose concentration was indicated by the display unit 19. Although the counter electrode 30 used was of metallic palladium, it could be replaced by one made of a silver-free palladium alloy.

Figure 3:
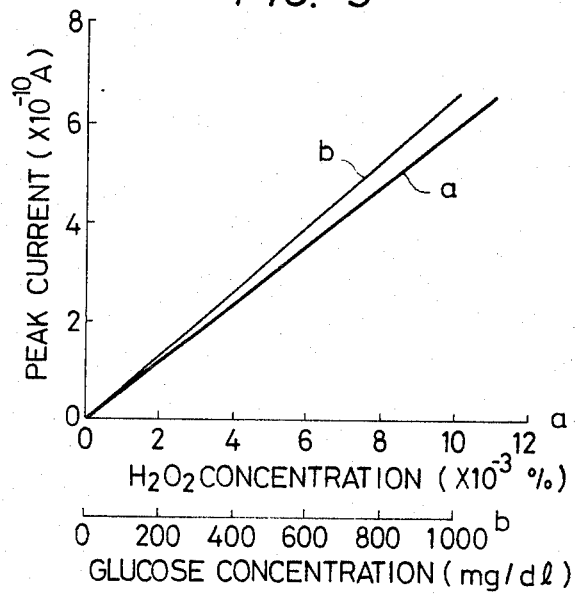
FIG. 3 is a graph showing typical working curves of hydrogen peroxide and glucose.

In FIG. 3 the curve b represents a working curve based on a glucose standard solution and a serum sample. The working curve was straight in the glucose concentration range from zero up to 1000 mg/dl.

Figure 5:
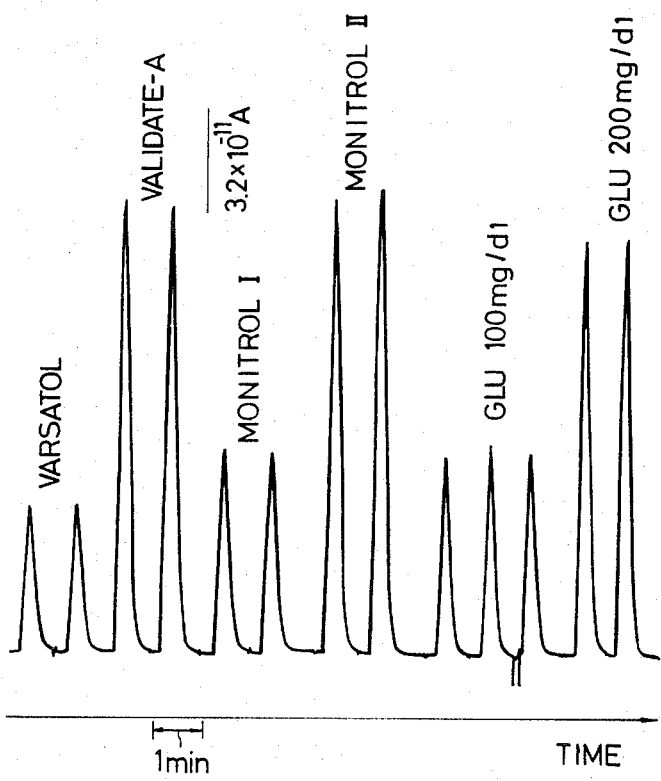
FIG. 5 is a graph showing example results of glucose concentration determination by the use of the sensor shown in FIG. 4.

FIG. 5 shows the results of blood sample determination by the use of the sensor of FIG. 4. "Varsatol", "Validate-A", "Monitorol I", and "Monitrol II" are trade designations of control serums. The adoption of the glucose sensor had little effect on the urea-nitrogen-detecting sensor and ensured good stability of the base line.

What is claimed is:

1. An analyzer including a urea-nitrogen-determining sensor having an enzyme membrane of immobilized urease and an electrochemical sensor arranged in a common flow passage, said electrochemical sensor comprising an electrically insulating body, a hydrogen peroxide-permeable membrane fitted to the body, said body holding an electrolyte therein, and a work electrode and a counter electrode both of which are disposed in said body, said counter electrode being made of a palladium-containing conductive material, whereby use of said palladium-containing conductive material as the counter electrode avoids deactivation of the urease by the material of said counter electrode.

2. An analyzer of claim 1, wherein said hydrogen peroxide-permeable membrane comprises an inner layer and an outer layer, said inner layer being permeable to hydrogen peroxide and said outer layer consisting of an immobilized oxidase layer.

3. An analyzer of claim 1, wherein the end portion of said body where a lead is connected to said work electrode is sealed up with a hydrophobic resin.

4. An analyzer of claim 1, wherein said work electrode is made of gold or platinum.

5. An analyzer of claim 1, wherein said counter electrode is made of metallic palladium.

6. An analyzer of claim 1, wherein said counter electrode is made of a silver-free palladium alloy.

7. An analyzer of claim 1, wherein said urea-nitrogen-determining sensor is positioned adjacent said electrochemical sensor in said common flow passage.

8. An analyzer of claim 1, wherein said urea-nitrogen-determining sensor and said electrochemical sensor are positioned in a common housing.

9. An analyzer comprising an urea-nitrogen-determining sensor having an enzyme membrane of immobilized urease, and an electrochemical sensor including a hydrogen peroxide-permeable membrane and capable of determining hydrogen peroxide concentrations, both said sensors being arranged to face a common flow passage, said electrochemical sensor including a work electrode and a counter electrode, the latter being formed of a palladium-containing conductive material, use of said palladium-containing conductive material for the counter electrode avoiding deactivation of the urease by the material of the counter electrode.

10. An analyzer of claim 9, wherein said electrochemical sensor consists of a glucose-determining sensor having a membrane composed of an outer layer of immobilized glucose oxidase and a hydrogen peroxide-permeable inner layer.

11. An analyzer of claim 9, wherein the work electrode is made of gold or platinum.

* * * * *